United States Patent

Brendel et al.

[11] Patent Number: 6,087,304
[45] Date of Patent: Jul. 11, 2000

[54] SUBSTITUTED 2-NAPHTHOYLGUANIDINES, PROCESS FOR THEIR PREPARATION, THEIR USE AS A MEDICAMENT OR DIAGNOSTIC, AND MEDICAMENT CONTAINING THEM

[75] Inventors: Joachim Brendel, Bad Vibel; Heinz-Werner Kleemann, Bischofsheim; Heinrich Christian Englert; Hans Jochen Lang, both of Hofheim; Jan-Robert Schwark, Frankfurt; Andreas Weichert, Egelsbach, all of Germany; Bansi Lal, Bombay, India

[73] Assignee: Hoechst Aktiengesellschaft, Frankfurt am Main, Germany

[21] Appl. No.: 08/857,631

[22] Filed: May 16, 1997

[30] Foreign Application Priority Data

May 29, 1996 [DE] Germany ............ 196 21 483

[51] Int. Cl.[7] .............. A01N 37/10; C07D 265/30; C07D 241/04; C07D 211/70
[52] U.S. Cl. .............. 504/244; 504/235; 504/223; 544/106; 544/392; 546/332
[58] Field of Search .............. 504/244, 235, 504/223; 544/106, 397; 546/332

[56] References Cited

U.S. PATENT DOCUMENTS 4,251,545 2/1981 Resnick .................. 424/324

FOREIGN PATENT DOCUMENTS

| 438667 | 5/1992 | European Pat. Off. . |
|---|---|---|
| 0 682 017 | 5/1995 | European Pat. Off. . |
| 0 810 205 | 5/1997 | European Pat. Off. . |
| 44 15 873 | 11/1995 | Germany . |
| 8-225513 | 9/1996 | Japan . |
| WO 94/26709 | 11/1994 | WIPO . |

*Primary Examiner*—D. Margaret Seaman
*Attorney, Agent, or Firm*—Finnegan, Henderson, Farabow, Garrett & Dunner, L.L.P.

[57] ABSTRACT

Substituted 2-naphthoylguanidines, process for their preparation, their use as a medicament or diagnostic, and medicament containing them Substituted 2-naphthoylguanidines of the formula I

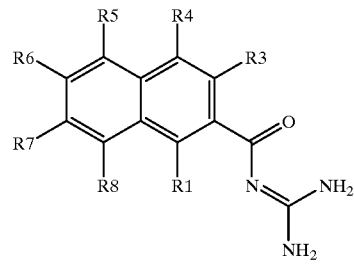

having the meanings indicated in claim 1 for R1 to R8, are suitable as antiarrhythmic pharmaceuticals having a cardioprotective component for infarct prophylaxis and infarct treatment and for the treatment of angina pectoris. They also preventively inhibit the pathophysiological processes in the formation of ischemically induced damage, in particular in the production of ischemically induced cardiac arrhythmias.

30 Claims, No Drawings

SUBSTITUTED 2-NAPHTHOYLGUANIDINES, PROCESS FOR THEIR PREPARATION, THEIR USE AS A MEDICAMENT OR DIAGNOSTIC, AND MEDICAMENT CONTAINING THEM

The invention relates to substituted 2-naphthoylguanidines of the formula I

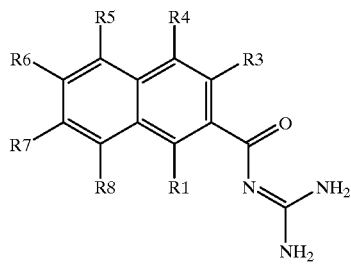

in which:
at least one of the substituents R1, R3, R4, R5, R6, R7 and R8 is
$XY_aWZ$ or $X'Y_aWZ'$;
X is O, S, NR(10) or CR(11)R(12);
R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
Y is alkylene having 1, 2, 3, 4, 5, 6, 7 or 8 $CH_2$ groups, where one of these $CH_2$ groups can be replaced by O, S, NR(13) or o-, p- or m-phenylene;
R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
a is zero or 1;
W is $CH_2$, $SO_2$, $S(=O)(=NH)$ or—if W does not immediately follow a heteroatom of the group $XY_a$—alternatively O or NR(14);
R(14) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
Z is $C(=O)R(15)$, $SO_2R(15)$ or—if W is not O or NR(14)—alternatively NR(16)R(17);
R(15) is $N=C(NH_2)_2$, NR(18)R(19), $N(CH_2)_bNR(18)R(19)$ or OR(20);
b is 2 or 3;
R(18) and R(19) independently of one another are H, alkyl having 1, 2, 3, 4, 5, 6, 7 or 8 carbon atoms or perfluoroalkyl having 1, 2, 3 or 4 carbon atoms; or
R(18) and R(19) together are 4 or 5 methylene groups, of which one $CH_2$ group can be replaced by oxygen, S, NH, N—$CH_3$, N-benzyl or N-(p-chlorophenyl);
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
R(16) and R(17) independently of one another are H, alkyl having 1, 2, 3, 4, 5, 6, 7 or 8 carbon atoms or perfluoroalkyl having 1, 2, 3 or 4 carbon atoms; or,
R(16) and R(17) together are 4 or 5 methylene groups, of which one $CH_2$ group can be replaced by oxygen, S, NH, N—$CH_3$, N-benzyl or N-(p-chlorophenyl);
X' is C=O, C(=O)NR(30), C(=O)O, SO, $SO_2$, $SO_2NR(30)$, OC=O, NR(30)C=O or $NR(30)SO_2$, where the linkage with the naphthalene ring in each case takes place via the left atom;
R(30) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
Z' is $C(=O)R(15)$, $SO_2R(15)$, an N-containing heterocycle having 1, 2, 3, 4, 5, 6, 7, 8 or 9 carbon atoms, where the N-containing heterocycle is linked via N or C and is unsubstituted or substituted by 1–3 substituents selected from the group consisting of F, Cl, Br, $CF_3$, methyl, methoxy and NR(21)R(22);
R(21) and R(22) independently of one another are H, alkyl having 1, 2, 3 or 4 carbon atoms or perfluoroalkyl having 1, 2, 3 or 4 carbon atoms;
R(15) is $N=C(NH_2)_2$, NR(18)R(19), $N(CH_2)_bNR(18)R(19)$ or OR(20);
R(18) and R(19) independently of one another are H, alkyl having 1, 2, 3, 4, 5, 6, 7 or 8 carbon atoms or perfluoroalkyl having 1, 2, 3 or 4 carbon atoms; or
R(18) and R(19) together are 4 or 5 methylene groups, of which one $CH_2$ group can be replaced by oxygen, S, NH, N—$CH_3$, N-benzyl or N-(p-chlorophenyl);
b is 2 or 3;
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms; or
Z'—if W is not O or NR(14)—is NR(16)R(17);
R(16) and R(17) independently of one another are H, alkyl having 1, 2, 3, 4, 5, 6, 7 or 8 carbon atoms or perfluoroalkyl having 1, 2, 3 or 4 carbon atoms; or
R(16) and R(17) together are 4 or 5 methylene groups, of which one $CH_2$ group can be replaced by oxygen, S, NH, N—$CH_3$, N-benzyl or N-(p-chlorophenyl);
and the other substituents R1, R3, R4, R5, R6, R7 and R8 in each case, which are still not allocated by the definitions given above,
independently of one another are H, F, Cl, Br, I, CN, $NO_2$, $CF_3$, $C_2F_5$ or $V_pQ_qU$;
V is O, S, SO, $SO_2$, NR(60), OC=O, C=O, C(=O)NR(60), C(=O)O or CR(66)R(67);
R(60), R(66) and R(67) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
p is zero or 1;
Q is alkylene having 1, 2, 3, 4, 5, 6, 7 or 8 $CH_2$ groups, where one of these $CH_2$ groups can be replaced by O, S, NR(68) or o-, p- or m-phenylene;
R(68) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
q is zero or 1;
U is H, alkyl having 1, 2, 3, 4, 5, 6 or 7 carbon atoms, cycloalkyl having 3, 4, 5, 6 or 7 carbon atoms, C(=O)R(65), $SO_2R(65)$, NR(61)R(62) or phenyl, which is unsubstituted or substituted by 1–3 substituents selected from the group consisting of F, Cl, Br, $CF_3$, methyl, methoxy and NR(63)R(64);
R(63) and R(64) independently of one another are H, alkyl having 1, 2, 3 or 4 carbon atoms or perfluoroalkyl having 1, 2, 3 or 4 carbon atoms;

R(65) is N=C(NH$_2$)$_2$, NR(61)R(62) or OR(60);
R(61) and R(62) independently of one another are H, alkyl having 1, 2, 3, 4, 5, 6, 7 or 8 carbon atoms or perfluoroalkyl having 1, 2, 3 or 4 carbon atoms; or
R(61) and R(62) together are 4 or 5 methylene groups, of which one CH$_2$ group can be replaced by oxygen, S, NH, N—CH$_3$, N-benzyl or N-(p-chlorophenyl); or
U is an N-containing heterocycle having 1, 2, 3, 4, 5, 6, 7, 8 or 9 carbon atoms, where the N-containing heterocycle is linked via N or C and is unsubstituted or substituted by 1–3 substituents selected from the group consisting of F, Cl, Br, CF$_3$, methyl, methoxy and NR(63)R(64);
but where at least one of the substituents R5, R6, R7 and R8 is not equal to hydrogen;
and their pharmaceutically tolerable salts.

Preferred compounds of the formula I are those in which:
to at least one of the substituents R1, R3, R4, R5, R6, R7 and R8 is XY$_a$WZ or X'Y$_a$WZ';
X is O, S, NR(10);
R(10) is H, alkyl having 1, 2, 3 or 4 carbon atoms, perfluoroalkyl having 1 or 2 carbon atoms or cycloalkyl having 3, 4, 5 or 6 carbon atoms;
Y is alkylene having 1, 2, 3, 4 or 5 CH$_2$ groups, where one of these CH$_2$ groups can be replaced by O, S, NR(13) or o-, p- or m-phenylene;
R(13) is H, alkyl having 1, 2, 3 or 4 carbon atoms or cycloalkyl having 3, 4, 5, or 6 carbon atoms;
a is zero or 1;
W is CH$_2$ or—if W does not immediately follow a heteroatom of the group XY$_a$—alternatively O or NR(14);
R(14) is H, alkyl having 1, 2, 3 or 4 carbon atoms;
Z is C(=O)R(15), SO$_2$R(15) or—if W is not O or NR(14)—alternatively NR(16)R(17);
R(15) is N=C(NH$_2$)$_2$, NR(18)R(19), N(CH$_2$)$_b$NR(18)R(19) or OR(20);
b is 2 or 3;
R(18) and R(19) independently of one another are H or alkyl having 1, 2, 3, 4 or 5 carbon atoms; or
R(18) and R(19) together are 4 or 5 methylene groups, of which one CH$_2$ group can be replaced by oxygen, S, NH, N—CH$_3$ or N-benzyl;
R(20) is H, alkyl having 1, 2, 3, 4, 5 or 6 carbon atoms;
R(16) and R(17) independently of one another are H, alkyl having 1, 2, 3, 4 or 5 carbon atoms or perfluoroalkyl having 1 or 2 carbon atoms; or
R(16) and R(17) together are 4 or 5 methylene groups, of which one CH$_2$ group can be replaced by oxygen, S, NH, N—CH$_3$, N-benzyl or N-(p-chlorophenyl);
X' is C(=O)NR(30), C(=O)O, SO$_2$NR(30), OC=O, NR(30)C=O or NR(30)SO$_2$, where the linkage with the naphthalene ring in each case takes place via the left atom;
R(30) is H, alkyl having 1, 2, 3 or 4 carbon atoms, perfluoroalkyl having 1 or 2 carbon atoms or cycloalkyl having 3, 4, 5 or 6 carbon atoms;
Z' is C(=O)R(15), SO$_2$R(15), an N-containing heterocycle having 1, 2, 3, 4, 5, 6, 7, 8 or 9 carbon atoms, where the N-containing heterocycle is linked via N or C and is unsubstituted or substituted by 1–3 substituents selected from the group consisting of F, Cl, Br, CF$_3$, methyl, methoxy and NR(21)R(22);
R(21) and R(22) independently of one another are H, alkyl having 1, 2, 3 or 4 carbon atoms;
R(15) is N=C(NH$_2$)$_2$, NR(18)R(19), N(CH$_2$)$_b$NR(18)R(19) or OR(20);
R(18) and R(19) independently of one another are H or alkyl having 1, 2, 3, 4 or 5 carbon atoms; or
R(18) and R(19) together are 4 or 5 methylene groups, of which one CH$_2$ group can be replaced by oxygen, S, NH, N—CH$_3$ or N-benzyl;
b is 2 or 3;
R(20) is H, alkyl having 1, 2, 3, 4, 5 or 6 carbon atoms; or
Z'—if W is not O or NR(14)—is NR(16)R(17);
R(16) and R(17) independently of one another are H, alkyl having 1, 2, 3, 4 or 5 carbon atoms or perfluoroalkyl having 1 or 2 carbon atoms; or
R(16) and R(17) together are 4 or 5 methylene groups, of which one CH$_2$ group can be replaced by oxygen, S, NH, N—CH$_3$, N-benzyl or N-(p-chlorophenyl);
and the other substituents R1, R3, R4, R5, R6, R7 and R8 in each case, which are still not allocated by the definitions given above,
independently of one another are H, F, Cl, Br, I, CN, NO$_2$, CF$_3$, C$_2$F$_5$ or V$_p$Q$_q$U;
V is O, S, SO$_2$, NR(60), OC=O, C=O, C(=O)NR(60), C(=O)O or CR(66)R(67);
R(60), R(66) and R(67) independently of one another are H, alkyl having 1, 2 or 3 carbon atoms, perfluoroalkyl having 1 or 2 carbon atoms or cycloalkyl having 3, 4, 5 or 6 carbon atoms;
p is zero or 1;
q is zero;
U is H, alkyl having 1, 2, 3 or 4 carbon atoms, cycloalkyl having 3, 4, 5 or 6 carbon atoms, C(=O)R(65), NR(61)R(62) or phenyl, which is unsubstituted or substituted by 1–3 substituents selected from the group consisting of F, Cl, Br, CF$_3$, methyl, methoxy and NR(63)R(64);
R(63) and R(64) independently of one another are H, alkyl having 1, 2, 3 or 4 carbon atoms;
R(65) is N=C(NH$_2$)$_2$ or OR(60);
R(61) and R(62) independently of one another are H, alkyl having 1, 2, 3 or 4 carbon atoms or perfluoroalkyl having 1 or 2 carbon atoms; or
R(61) and R(62) together are 4 or 5 methylene groups, of which one CH$_2$ group can be replaced by oxygen, S, NH, N—CH$_3$ or N-benzyl; or
U is an N-containing heterocycle having 1, 2, 3, 4, 5, 6, 7, 8 or 9 carbon atoms, where the N-containing heterocycle is linked via N or C and is unsubstituted or substituted by 1–3 substituents selected from the group consisting of F, Cl, Br, CF$_3$, methyl, methoxy and NR(63)R(64);
but where at least one of the substituents R5, R6, R7 and R8 is not equal to hydrogen;
and their pharmaceutically tolerable salts.

Particularly preferred compounds of the formula I are those in which:
at least one of the substituents R1, R3, R4, R5, R6, R7 and R8 is XY$_a$WZ or X'Y$_a$WZ';
X is 0;
Y is alkylene having 1, 2, 3, 4 or 5 CH$_2$ groups, where one of these CH$_2$ groups can be replaced by o-, p- or m-phenylene;
a is zero or 1;
W is CH$_2$ or—if W does not immediately follow a heteroatom of the group XY$_a$—alternatively O or NR(14);
R(14) is H or methyl;

Z is C(=O)R(15), or—if W is not O or NR(14)—alternatively NR(16)R(17);
R(15) is N=C(NH$_2$)$_2$, NR(18)R(19), or OR(20);
R(18) and R(19) independently of one another are H or alkyl having 1, 2, 3 or 4 carbon atoms; or
R(18) and R(19) together are 4 or 5 methylene groups, of which one CH$_2$ group can be replaced by oxygen, NH, N—CH$_3$ or N-benzyl;
R(20) is H or alkyl having 1, 2 or 3 carbon atoms;
R(16) and R(17) independently of one another are H or alkyl having 1, 2, 3 or 4 carbon atoms; or
R(16) and R(17) together are 4 or 5 methylene groups, of which one CH$_2$ group can be replaced by oxygen, S, NH, N—CH$_3$, N-benzyl or N-(p-chlorophenyl);
X' is C(=O)NR(30), C(=O)O or SO$_2$NR(30), where the linkage with the naphthalene ring in each case takes place via the left atom;
R(30) is H or methyl;
Z' is C(=O)R(15), an N-containing heterocycle having 1, 2, 3, 4, 5, 6, 7, 8 or 9 carbon atoms, where the N-containing heterocycle is linked via N or C;
R(15) is N=C(NH$_2$)$_2$, NR(18)R(19) or OR(20);
R(18) and R(19) independently of one another are H or alkyl having 1, 2, 3 or 4 carbon atoms; or
R(18) and R(19) together are 4 or 5 methylene groups, of which one CH$_2$ group can be replaced by oxygen, NH, N—CH$_3$, or N-benzyl;
R(20) is H or alkyl having 1, 2 or 3 carbon atoms; or
Z' if W is not O or NR(14)—is NR(16)R(17);
R(16) and R(17) independently of one another are H or alkyl having 1, 2, 3 or 4 carbon atoms; or
R(16) and R(17) together are 4 or 5 methylene groups, of which one CH$_2$ group can be replaced by oxygen, S, NH, N—CH$_3$ or N-benzyl;
and the other substituents R1, R3, R4, R5, R6, R7 and R8 in each case, which are still not allocated by the definitions given above,
independently of one another are H, F, Cl, Br, I, CF$_3$ or V$_p$Q$_q$U;
V is O, SO$_2$, NR(60), OC=O, C(=O)NR(60), C(=O)O or CR(66)R(67);
R(60), R(66) and R(67) independently of one another are H or alkyl having 1, 2 or 3 carbon atoms;
p is zero or 1;
q is zero;
U is H, alkyl having 1, 2 or 3 carbon atoms, C(=O)R(65), NR(61)R(62) or phenyl, which is unsubstituted or substituted by 1–3 substituents selected from the group consisting of F, Cl, Br, CF$_3$, methyl, methoxy and NR(63)R(64);
R(63) and R(64) independently of one another are H or methyl;
R(65) is N=C(NH$_2$)$_2$; or
U is an N-containing heterocycle having 1, 2, 3, 4, 5, 6, 7, 8 or 9 carbon atoms, where the N-containing heterocycle is linked via N or C;
but where at least one of the substituents R5, R6, R7 and R8 is not equal to hydrogen;
and their pharmaceutically tolerable salts.

If the compounds of the formula I contain one or more centers of asymmetry, these can have either the S or the R configuration. The compounds can be present as optical isomers, as diastereomers, as racemates or as mixtures thereof.

The alkyl radicals and perfluoroalkyl radicals designated can be either straight-chain or branched.

N-containing heterocycles having 1, 2, 3, 4, 5, 6, 7, 8 or 9 carbon atoms include, in particular, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, isoindolyl, benzimidazolyl, indazoyl, quinolyl, isoquinolyl, phthalazinyl, quinoxalinyl, quinazolinyl, cinnolinyl.

The N-containing heterocycles pyrrolyl, imidazolyl, quinolyl, pyrazolyl, pyridyl, pyrazinyl, pyrimidinyl and pyridazinyl are particularly preferred.

The invention furthermore relates to a process for the preparation of the compound I, which comprises reacting a compound of the formula II

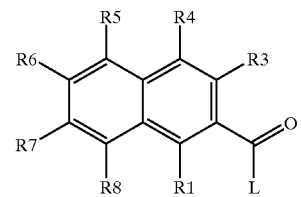

in which L is an easily nucleophilically substitutable leaving group, and the other substituents have the abovementioned meaning, with guanidine.

The activated acid derivatives of the formula II in which L is an alkoxy group, preferably a methoxy group, a phenoxy group, a phenylthio, methylthio or 2-pyridylthio group, or a nitrogen heterocycle, preferably 1-imidazolyl, are advantageously obtained in a manner known per se from the underlying carbonyl chlorides (formula II, L=Cl), which for their part can in turn be prepared in a manner known per se from the underlying carboxylic acids (formula II, L=OH), for example using thionyl chloride.

In addition to the carbonyl chlorides of the formula II(L=Cl), other activated acid derivatives of the formula II can also be prepared in a manner known per se directly from the underlying naphthoic acid derivatives (formula II, L=OH), such as, for example, the methyl esters of the formula II where L=OCH$_3$ by treatment with gaseous HCl in methanol, the imidazolides of the formula II by treatment with carbonyldiimidazole [L=1-imidazolyl, Staab, Angew. Chem. Int. Ed. Engl. 1, 351–367 (1962)], the mixed anhydrides II using Cl—COOC$_2$H$_5$ ortosyl chloride in the presence of triethylamine in an inert solvent; the activation of the carboxylic acids can also be carried out with dicyclohexylcarbodiimide (DCC) or with O-[(cyano(ethoxy-carbonyl) methylene)amino]-1,1,3,3-tetramethyluronium tetrafluoborate ("TOTU") [Proceedings of the 21st European Peptide Symposium, Peptides 1990, Editors E. Giralt and D. Andreu, Escom, Leiden, 1991]. A number of suitable methods for the preparation of activated carboxylic acid derivatives of the formula II are given under details of source literature in J. March, Advanced Organic Chemistry, Third Edition (John Wiley & Sons, 1985), p. 350.

The reaction of an activated carboxylic acid derivative of the formula II with guanidine is carried out in a manner known per se in a protic or aprotic polar but inert organic solvent. Methanol, isopropanol or THF from 20° C. to the boiling point of these solvents have proven suitable in the reaction of the methyl naphthoates (II, L=OMe) with guanidine. In most reactions of compounds II with salt-free guanidine, the reaction was advantageously carried out in aprotic inert solvents such as THF, dimethoxyethane, dioxane or DMF. However, water can also be used as a solvent in the reaction of II with guanidine if a base such as, for example, NaOH is used.

If L=Cl, the reaction is advantageously carried out with the addition of an acid scavenger, for example in the form of excess guanidine for binding the hydrohalic acid.

Some of the underlying naphthoic acid derivatives of the formula II are known and described in the literature. The unknown compounds of the formula II can be prepared by methods known from the literature.

In general, carboxylguanidines I are weak bases and can bind acid with the formation of salts. Possible acid addition salts are salts of all pharmacologically tolerable acids, for example halides, in particular hydrochlorides, lactates, sulfates, citrates, tartrates, acetates, phosphates, methanesulfonates, p-toluenesulfonates, maleates and fumarates.

The compounds I are substituted acylguanidines. The most prominent representative of the acylguanidines is the pyrazine derivative amiloride, which is used in therapy as a potassium-sparing diuretic. Numerous other compounds of the amiloride type are described in the literature, such as, for example, dimethylamiloride or ethylisopropylamiloride.

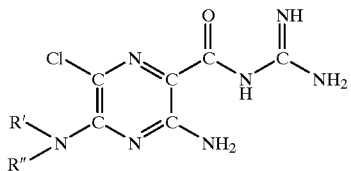

Amiloride: R', R"=H
Dimethylamiloride: R', R'=CH$_3$
Ethylisopropylamiloride: R'=C$_2$H$_5$, R"=CH(CH$_3$)$_2$ Investigations have moreover been disclosed which point to antiarrhythmic properties of amiloride [Circulation 79,1257–63 (1989)]. Obstacles to wide use as an antiarrhythmic are, however, that this effect is only slightly pronounced and occurs accompanied by a hypotensive and saluretic action and these side effects are undesired in the treatment of cardiac arrhythmias.

Indications of antiarrhythmic properties of amiloride were also obtained in experiments on isolated animal hearts [Eur. Heart J. 9 (suppl.1): 167 (1988) (book of abstracts)]. For instance, it was found in rat hearts that an artificially induced ventricular fibrillation could be suppressed completely by amiloride. The abovementioned amiloride derivative ethylisopropylamiloride was even more potent than amiloride in this model.

U.S. Pat. No. 4,251,545 discloses 1-naphthoylguanidines which are substituted in the 4-position by long-chain alkoxy groups. Use as fungicides in plant protection is described for these compounds.

The Offenlegungsschrift WO 94/26709 claims 2-naphthoylguanidines which carry hydrogen atoms in the positions corresponding to the radicals R5, R6, R7 and R8.

In addition to bicyclic heteroaroylguanidines, EP-A 682 017 (HOE 94/F123) also describes some naphthoylguanidines, the substituents R1 to R8, however, having other meanings than in the present application.

In these patent publications WO 94/26709 and EP-A 682 017 (HOE 94/F123), the only example shown is unsubstituted 2-naphthoylguanidine.

The compounds known from the publications mentioned, however, do not fulfill all requirements which are necessary for the development of a medicament from a pharmacologically active compound. For example, better absorption, more favorable half-life times, better water solubility, lower toxicity or higher selectivity would thus be desirable. This is achieved by the compounds according to the invention, which additionally exhibit no undesired and disadvantageous salidiuretic properties, but very good antiarrhythmic properties, such as are important, for example, for the treatment of diseases which are caused by oxygen deficiency. As a result of their pharmacological properties, the compounds, as antiarrhythmic pharmaceuticals having a cardioprotective component, are outstandingly suitable for infarct prophylaxis and infarct treatment and for the treatment of angina pectoris, where they also preventively inhibit or greatly decrease the pathophysiological processes in the formation of ischemically induced damage, in particular in the production of ischemically induced cardiac arrhythmias. Because of their protective actions against pathological hypoxic and ischemic situations, the compounds of the formula I according to the invention can be used as a result of inhibition of the cellular Na$^+$/H$^+$ exchange mechanism as pharmaceuticals for the treatment of all acute or chronic damage caused by ischemia or primary or secondary diseases induced thereby. This relates to their use as pharmaceuticals for surgical interventions, for example in organ transplants, where the compounds can be used both for the protection of the organs in the donor before and during removal, for the protection of removed organs, for example during treatment with or storage thereof in physiological bath fluids, and also during transfer to the body of the recipient. The compounds are also useful protective pharmaceuticals during the performance of angioplastic surgical interventions, for example in the heart and in peripheral vessels. In accordance with their protective action against ischemically induced damage, the compounds are also suitable as pharmaceuticals for the treatment of ischemias of the nervous system, in particular the CNS, where they are suitable, for example, for the treatment of stroke or of cerebral edema. Moreover the compounds of the formula I according to the invention are also suitable for the treatment of forms of shock, such as, for example, allergic, cardiogenic, hypovolemic and bacterial shock.

Moreover, the compounds of the formula I according to the invention are distinguished by potent inhibitory action on the proliferation of cells, for example fibroblast cell proliferation and the proliferation of vascular smooth muscle cells. The compounds of the formula I can therefore be considered as useful therapeutics for diseases in which cell proliferation is a primary or secondary cause, and can therefore be used as antiatherosclerotics, agents against diabetic late complications, cancers, fibrotic diseases such as pulmonary fibrosis, fibrosis of the liver or fibrosis of the kidneys, organ hypertrophies and hyperplasias, in particular in prostate hyperplasia or prostate hypertrophy.

The compounds according to the invention are active inhibitors of the cellular sodium-proton antiporter (Na$^+$/H$^+$ exchanger), which is also raised in numerous diseases (essential hypertension, atherosclerosis, diabetes, etc.) in those cells which are easily accessible to measurements, such as, for example, in erythrocytes, platelets or leucocytes. The compounds according to the invention are therefore suitable as outstanding and simple scientific tools, for example in their use as diagnostics for the determination and differentiation of certain forms of hypertension, but also of atherosclerosis, diabetes, proliferative diseases etc. Moreover, the compounds of the formula I are suitable for preventive therapy for the prevention of the formation of high blood pressure, for example, essential hypertension.

It has additionally been found that compounds of the formula I have a favorable effect on serum lipoproteins. It is generally recognized that for the formation of arteriosclerotic vascular changes, in particular of coronary heart disease, excessively high blood lipid values, so-called hyperlipoproteinemias, are a significant risk factor. For the prophylaxis and the regression of atherosclerotic changes, the lowering of raised serum lipoproteins is therefore extremely important. Beside the reduction of the total serum cholesterol, the lowering of the proportion of specific atherogenic lipid fractions of this total cholesterol, in particular of the low density lipoproteins (LDL) and of the very low density lipoproteins (VLDL) is particularly important, as these lipid fractions are an antherogenic risk factor. In contrast, high density lipoproteins are ascribed a protective function against coronary heart disease. Accordingly, hypolipidemics should be able not only to lower the total cholesterol, but in particular to lower the VLDL and LDL serum cholesterol fractions. It has now been found that compounds of the formula I have valuable therapeutically utilizable properties with respect to the affect on the serum lipid levels. Thus they significantly reduce the increased serum concentration of LDL and VLDL, as are to be observed, for example, due to increased dietetic intake of a cholesterol- and lipid-rich diet or in pathological metabolic changes, for example genetically related hyperlipidemias. They can therefore be used for the prophylaxis and for the regression of atherosclerotic changes in that they exclude a causal risk factor. These include not only the primary hyperlipidemias, but also certain secondary hyperlipidemias, such as occur, for example, in diabetes. Moreover, the compounds of the formula I lead to a distinct reduction of the infarct induced by metabolic anomalies and in particular to a significant reduction of the induced infarct size and its degree of severity. Compounds of the formula I furthermore lead to effective protection against endothelial damage induced by metabolic anomalies. With this protection of the vessels against the endothelial dysfunction syndrome, compounds of the formula I are valuable pharmaceuticals for the prevention and for the treatment of coronary vascular spasms, of atherogenesis and of atherosclerosis, of left-ventricular hypertrophy and of dilated cardiomyopathy, and of thrombotic disorders.

The compounds mentioned are therefore advantageously used for the production of a medicament for the treatment of hypercholesterolemia; for the production of a medicament for the prevention of atherogenesis; for the production of a medicament for the prevention and treatment of atherosclerosis, for the production of a medicament for the prevention and treatment of illnesses which are caused by raised cholesterol levels, for the production of a medicament for the prevention and treatment of illnesses which are caused by endothelial dysfunction, for the production of a medicament for the prevention and treatment of atherosclerosis-induced hypertension, for the production of a medicament for the prevention and treatment of atherosclerosis-induced thromboses, for the production of a medicament for the prevention and treatment of hypercholesterolemia- and endothelial dysfunction-induced ischemic damage and postischemic reperfusion damage, for the production of a medicament for the prevention and treatment of hypercholestrolemia- and endothelial dysfunction-induced cardiac hypertrophies and cardiomyopathies, for the production of a medicament for the prevention and treatment of hypercholesterolemia- and endothelial dysfunction-induced coronary vascular spasms and myocardial infarcts, for the production of a medicament for the treatment of the illnesses mentioned in combinations with hypertensive substances, preferably with angiotensin-converting enzyme (ACE) inhibitors and angiotensin receptor antagonists, a combination of an NHE inhibitor of the formula I with a hypolipidemic active compound, preferably with an HMG-CoA reductase inhibitor (e.g. lovastatin or pravastatin), the latter contributing a hypolipidemic action and thereby increasing the hypolipidemic properties of the NHE inhibitor of the formula I and proving to be a favorable combination with increased action and reduced use of active compound.

The administration is therefore also claimed of sodium-proton exchange inhibitors of the formula I as pharmaceuticals for the lowering of increased blood lipid levels, and the combination of sodium-proton exchange inhibitors with pharmaceuticals having hypotensive and/or hypolipidemic activity.

Pharmaceuticals which contain a compound I can be administered orally, parenterally, intravenously, rectally or by inhalation, the preferred administration being dependent on the particular type of the disease. The compounds I can be used on their own or together with pharmaceutical auxiliaries, to be precise both in veterinary and in human medicine.

The auxiliaries which are suitable for the desired pharmaceutical formulation are familiar to the person skilled in the art. In addition to solvents, gelling agents, suppository bases, tabletting auxiliaries and other active compound excipients, antioxidants, dispersants, emulsifiers, antifoams, flavor correctants, preservatives, solubilizers or colorants, for example, can be used.

For a form for oral administration, the active compounds are mixed with the additives suitable for this purpose, such as excipients, stabilizers or inert diluents, and are brought by the customary methods into the suitable administration forms, such as tablets, coated tablets, hard gelatine capsules, or aqueous, alcoholic or oily solutions. Inert excipients which can be used are, for example, gum arabic, magnesia, magnesium carbonate, potassium phosphate, lactose, glucose or starch, in particular cornstarch. Preparation can be carried out here both as dry and as moist granules. Suitable oily excipients or solvents are, for example, vegetable or animal oils, such as sunflower oil or fish liver oil.

For subcutaneous or intravenous administration, the active compounds are brought into solution, suspension or emulsion, if desired using the substances customary for this purpose such as solubilizers, emulsifiers or other auxiliaries. Suitable solvents are, for example: water, physiological saline solution or alcohols, for example ethanol, propanol, glycerol, and also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of these solvents.

If required, the formulation can also contain still other pharmaceutical auxiliaries such as surfactants, emulsifiers and stabilizers as well as a propellant. Such a preparation contains the active compound customarily in a concentration from about 0.1 to 10, in particular from about 0.3 to 3% by weight.

The dose of the active compound of the formula I to be administered and the frequency of administration depend on the potency and duration of action of the compounds used and additionally on the type and severity of the disease to be treated and on the sex, age, weight and individual responsiveness of the mammal to be treated. On average, the daily dose of a compound of the formula I in a patient of weight about 75 kg is at least 0.001 mg/kg, preferably 0.01 mg/kg, to at most 10 mg/kg, preferably 1 mg/kg of body weight. In acute episodes of the disease, for example immediately after suffering a cardiac infarct, even higher and in particular more frequent doses may be necessary, for example up to 4 individual doses per day. In particular when administered i.v., for example in the case of an infarct patient in the intensive care unit, up to 200 mg per day may be necessary.

Experimental Section

| List of abbreviations: | |
|---|---|
| CDI | Carbonyldiimidazole |
| DMF | N,N-dimethylformamide |
| RT | Room temperature |
| m.p. | Melting point |
| FC | Flash chromatography |
| THF | Tetrahydrofuran |
| eq. | Equivalent |
| EA | Ethyl acetate (EtOAc) |

General Procedures for the Preparation of Naphthoylguanidines (I)

Variants 1 A: From Naphthoic Acids (II, L=OH)

1.0 eq. of the naphthoic acid derivative of the formula II is dissolved or suspended in anhydrous THF (5 ml/mmol) and then treated with 1.2 eq. of carbonyldiimidazole. After stirring for 2 hours at RT, 5.0 eq. of guanidine are introduced into the reaction solution. After stirring overnight, the THF is distilled off under reduced pressure (in a rotary evaporator), the residue is treated with water and the corresponding guanidine (formula I) is filtered off. The carboxylguanidines thus obtained can be converted into the corresponding salts by treating with aqueous, methanolic or ethereal hydrochloric acid or other pharmacologically tolerable acids.

Variant 1 B: From Alkyl Naphthoates (II, L=O-alkyl)

1.0 eq. of the alkyl carboxylates of the formula II and 5.0 eq. of guanidine (free base) are dissolved or suspended in isopropanol or in THF and boiled under reflux (typical reaction time 2 to 5 h) until conversion is complete (thin-layer checking). The solvent is distilled off under reduced pressure (rotary evaporator), and the residue is taken up in EA and washed 3 times with NaHCO$_3$ solution. It is dried over Na$_2$SO$_4$, the solvent is distilled off in vacuo and the residue is chromatographed on silica gel using a suitable eluent, e.g. EA/MeOH 5:1.

(For Salt Formation Compare Variant A)

EXAMPLE 1

6-(2-diethylaminoethoxy)-2-naphthoylguanidine dihydrochloride

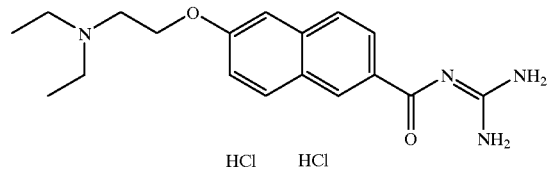

a) 6-Hydroxy-2-naphthoic acid is heated under reflux for 2 h in anhydrous methanol which had previously been saturated with HCl gas. The mixture is concentrated, the residue is recrystallized once each from methanol and from acetone and methyl 6-hydroxy-2-naphthoate is obtained.

b) 3.2 g of methyl 6-hydroxy-2-naphthoate and 1.28 g of sodium methoxide are stirred at 40° C. under N$_2$ for 20 min in 50 ml of DMF. 3.65 g of diethylaminoethyl chloride are then added and the mixture is stirred at 40° C. for a further 2 h. The DMF is stripped off on a rotary evaporator, the residue is taken up in dilute hydrochloric acid and the mixture is extracted with ethyl acetate. The aqueous phase is rendered alkaline with sodium hydroxide solution and extracted again with ethyl acetate. After concentrating this extract, 2.7 g of methyl 6-(2-diethylaminoethoxy)-2-naphthoate are obtained.

c) 3.1 g of methyl 6-(2-diethylaminoethoxy)-2-naphthoate and 1.2 g of KOH are dissolved in 20 ml of methanol and heated under reflux for 3 h. After stripping off the methanol, the residue is dissolved in 20 ml of water and adjusted to pH 2.5 using 10% hydrochloric acid. The precipitate which is deposited is filtered off with suction, and 2.7 g of 6-(2-diethylaminoethoxy)-2-naphthoic acid are obtained.

d) 0.79 g of CDI are added to a suspension of 1.0 g of 6-(2-diethyl-aminoethoxy)-2-naphthoic acid in 20 ml of DMF, and the reaction mixture is stirred at RT overnight. The mixture is then treated with 1.0 g of guanidine, again stirred overnight and concentrated, and the residue is stirred with 20 ml of water. The precipitate formed is filtered off with suction, suspended in ether and, after addition of ethereal hydrochloric acid, the mixture is stirred for a further 3 h. After filtering off with suction, 0.9 g of 6-(2-diethylaminoethoxy)-2-naphthoylguanidine dihydrochloride is obtained;

m.p.: 225° C.

$^1$H-NMR (DMSO-d6): δ [ppm]=1.3 (6H),3.25 (4H),3.6 (2H),4.55 (2H), 7.4 (1H), 7.55 (1H), 8.05 (2H), 8.15 (1H), 8.65 (2H), 8.9 (2H), 8.95 (1H), 10.5 (1H), 12.3 (1H).

EXAMPLE 2

6-(2-Diisopropylaminoethoxy)-2-naphthoylguanidine dihydrochloride

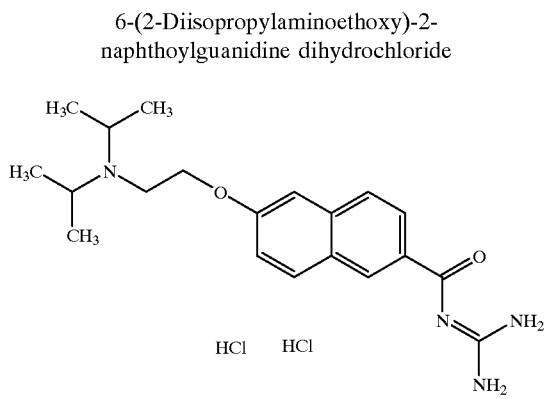

a) Analogously to Example 1 b, 4.2 g of methyl 6-(2-diisopropyl-aminoethoxy)-2-naphthoate are obtained from 3.2 g of methyl 6-hydroxy-2-naphthoate and 4.4 g of diisopropylaminoethyl chloride (obtained from the hydrochloride using sodium hydroxide solution and extraction with ether).

b) 3.6 g of methyl 6-(2-diisopropylaminoethoxy)-2-naphthoate and 1.8 g of KOH are heated under reflux for 5 h in methanol. After concentrating and taking up the residue in water, the mixture is adjusted to pH 6 using hydrochloric acid, whereupon the product precipitates. 3.3 g of 6-(2-diisopropylaminoethoxy)-2-naphthoic acid are obtained;

m.p.: 183–184° C.

c) 3.3 g of 6-(2-diisopropylaminoethoxy)-2-naphthoic acid and 3.1 g of CDI are suspended in THF and the mixture is stirred overnight. After addition of 3.2 g of guanidine, it is stirred at RT for a further 4 h, the solvent is largely stripped off and the residue is poured onto 170 ml of water. The product which is deposited is filtered off with suction, dissolved in 150 ml of methanol and 50 ml of ethyl acetate and treated with excess ethereal hydrochloric acid. 1.8 g of 6-(2-diisopropyl-aminoethoxy)-2-naphthoylguanidine dihydrochloride are obtained;

m.p.: 259–260° C.

$^1$H-NMR (DMSO-d6): δ [ppm]=1.5 (12H), 3.7 (2H), 3.9 (2H), 4.7 (2H ), 7.5 (1H),7.6 (1H), 8.1 (2H), 8.3 (1H), 8.8 (2H), 9.0 (2H), 9.1 (1H), 9.9 (1H), 12.5 (1H).

EXAMPLE 3

6-[2-(4-Morpholinyl)ethoxy]-2-naphthoylguanidine dihydrochloride

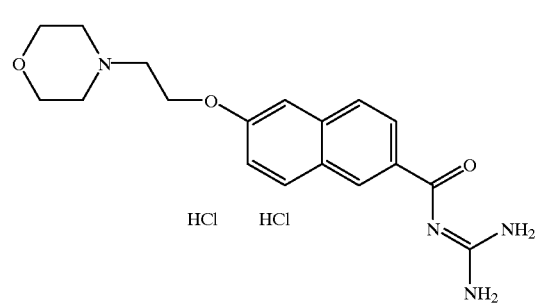

a) 6.4 g of methyl 6-hydroxy-2-naphthoate and 2.56 g of sodium methoxide are stirred under $N_2$ at 40° C. for 30 min in 100 ml of DMF. 8.04 g of N-(2-chloroethyl)morpholine are then added and the mixture is stirred at 80° C. for 2 h. The reaction mixture is poured onto water, and the precipitate which is deposited is filtered off with suction. 9.2 g of methyl 6-[2-(4-morpholinyl)ethoxy]-2-naphthoate are obtained.

b) By alkaline hydrolysis of the methyl 6-[2-(4-morpholinyl)ethoxy]-2-naphthoate analogously to Example 1 c and subsequent reaction with CDI and guanidine according to the general procedure, variant 1 a, 6-[2-(4-morpholinyl)ethoxy]-2-naphthoylguanidine dihydrochloride is obtained;

m.p. 254–256° C.

EXAMPLE 4

6-(Guanidinocarbonylmethoxy)-2-naphthoylguanidine dihydrochloride

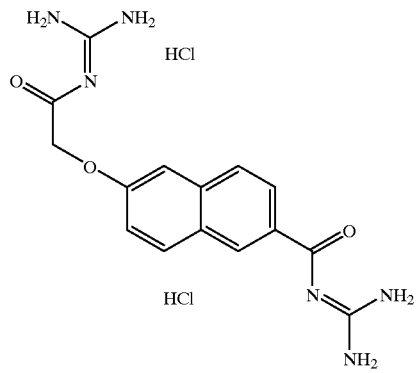

a) 3.2 g of methyl 6-hydroxy-2-naphthoate and 1.28 g of sodium methoxide are stirred under $N_2$ at 40° C. for 15 min in 50 ml of DMF. 4.1 g of methyl bromoacetate are then added and the reaction mixture is stirred at 70° C. for 6 h. It is poured onto 100 ml of water, and the precipitate which is deposited is filtered off with suction and recrystallized from isopropanol. 2.3 g of methyl 6-methoxycarboxylmethoxy-2-naphthoate are obtained;

m.p. 138–139° C.

b) 2.3 g of methyl 6-methoxycarbonylmethoxy-2-naphthoate and 2.3 g of KOH are heated under reflux for 3 h in 100 ml of water and 10 ml of DMF. The mixture is then acidified to pH 0.3 using hydrochloric acid, and the precipitate which is deposited is filtered off with suction at RT. 1.7 g of methyl 6-carboxymethoxy-2-naphthoate are obtained;

m.p.>285° C.

c) 1.7 g of methyl 6-carboxymethoxy-2-naphthoate and 3.1 g of CDl are dissolved in 50 ml of DMF and stirred at RT overnight. After addition of 2.85 g of guanidine, the mixture is again stirred at RT overnight, the solvent is distilled off in vacuo and the residue is stirred with water. The precipitate formed is filtered off with suction, dissolved in methanol and treated with ethyl acetate/HCl. 1.5 g of 6-guanidinocarbonylmethoxy- 2-naphthoylguanidine dihydrochloride are obtained;

m.p.: 264–267° C.

$^1$H-NMR (DMSO-d6): δ [ppm]=5.0 (2H), 7.5–8.1 (5H), 8.4–8.8 (8H), 8.9 (1H), 11.7 (1H), 12.2 (1H).

thereto, the mixture is stirred for 3 h and concentrated, and the residue is stirred with water. The product which is deposited is filtered off with suction and 1.35 g of 6-methoxycarbonyl-naphthalene-2-N-(3-pyridylmethyl) carboxamide are obtained.

c) 1.2 g of 6-methoxycarbonyinaphthalene-2-N-(3-pyridylmethyl)-carboxamide and 0.5 g of KOH are suspended in 25 ml of methanol and the mixture is stirred at RT for 4 days. It is concentrated on a rotary evaporator, the residue is stirred with 20 ml of methylene chloride, and the precipitate is filtered off with suction and dissolved in 20 ml of water. After acidifying to pH 6.2, the product is deposited, and 0.8 g of 6-carboxynaphthalene-2-N-(3-pyridylmethyl) carboxamide is obtained: m.p.>250° C.

d) 0.75 g of 6-carboxynaphthalene-2-N-(3-pyridylmethyl) carboxamide are reacted with CDl and guanidine analogously to Example 1 d. 0.5 g of 6-(3-pyridylmethylaminocarbonyl)-2-naphthoylguanidine dihydrochloride is obtained; m.p.: 285° C.

$^1$H-NMR (DMSO-d6): δ [ppm]=4.75 (2H), 7.95 (2H), 8.15 (4H), 8.45 (1H), 8.55–9.0 (7H), 9.65 (1H) 12.4 (1H).

EXAMPLE 6

6-[2-(Guanidinocarbonyloxy)ethylaminocarbonyl]-2-naphthoylguanidine dihydrochloride

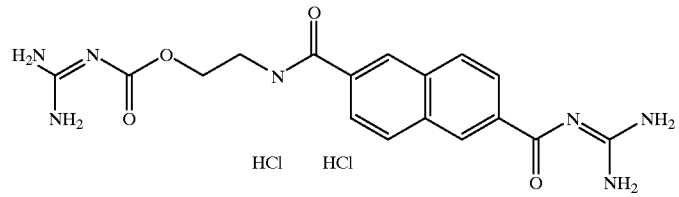

EXAMPLE 5

6-(3-Pyridylmethylaminocarbonyl)-2-naphthoylguanidine dihydrochloride

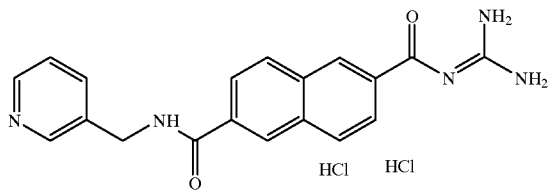

a) 4.9 g of dimethyl naphthalene-2,6-dicarboxylate and 0.7 g of KOH (85% strength) are dissolved in 150 ml of methylene chloride and 30 ml of methanol and the mixture is stirred at room temperature overnight. The potassium salt which is deposited is filtered off with suction, dissolved in water and acidified with hydrochloric acid. After filtering off the precipitate with suction, 2.55 g of naphthalene-2,6-dicarboxylic acid monomethyl ester are obtained.

b) 2.07 g of naphthalene-2,6-dicarboxylic acid monomethyl ester and 1.62 g of CDl are stirred at RT overnight in 25 ml of DMF. 1.08 g of 3-picolylamine are then added a) 2.1 g of naphthalene-2,6-dicarboxylic acid monomethyl ester and 25 ml of ethanolamine are heated at 150° C. for 3 h. The excess ethanolamine is distilled off in vacuo, and the residue is dissolved in water and the mixture is extracted with ethyl acetate. After acidifying the aqueous phase, the product which is deposited is filtered off with suction and recrystallized from ethanol. 1.2 g of 6-(2-hydroxyethylaminocarbonyl)-2-naphthoic acid are obtained.

b) 1.2 g of 6-(2-hydroxyethylaminocarbonyl)-2-naphthoic acid and 1.9 g of CDl are dissolved in 13 ml of DMF and stirred at RT overnight. 2.2 g of guanidine are added thereto, the mixture is stirred overnight again and concentrated, the residue is treated with water and the precipitate which is deposited is filtered off. 0.94 g of 6-[2-(guanidinocarbonyloxy)-ethylaminocarbonyl]-2-naphthoylguanidine is obtained; m.p. about 205° C. By dissolving it in 2 mol equivalents of dilute hydrochloric acid and subsequent freeze drying, the corresponding dihydrochloride is obtained; m.p. about 270° C.

EXAMPLE 7

6-{2-[4-(4-Chlorophenyl)-1-piperazinyl]-ethoxy}-2-naphthoylguanidine dihydrochloride

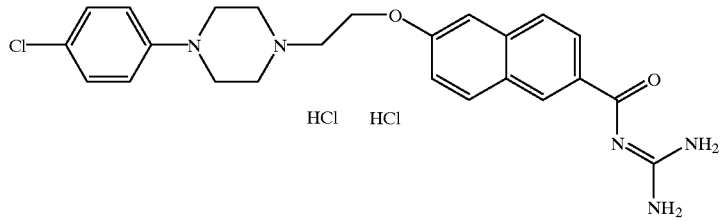

a) 2.11 g of methyl 6-hydroxy-2-naphthoate and 0.84 g of sodium methoxide are stirred under $N_2$ at 40° C. for 30 min in 50 ml of DMF. 4.6 g of 4-(p-chlorophenyl) piperazinoethyl chloride are then added and the reaction mixture is stirred at 40° C. for 8 h. It is diluted with 350 ml of methanol and the precipitate which is deposited is filtered off with suction. It is dissolved in 80 ml of DMF and 10 ml of water, and the mixture is treated with 3.8 g of KOH and stirred at 100° C. for 10 h. The DMF is largely stripped off on a rotary evaporator, the residue is poured onto water and acidified, and the resulting precipitate is filtered off with suction. 2.5 g of 6-{2-[4-(4-chlorophenyl)-1-piperazinyl] ethoxy}-2-naphthoic acid are obtained; m.p. 197–199° C.

b) 2.4 g of 6-{2-[4-(4-chlorophenyl)-1-piperazinyl]-ethoxy}-2-naphthoic acid are reacted with CDI and guanidine according to the general procedure (variant 1 a). 1.4 g of 6-{2-[4-(4-chlorophenyl)-1-piperazinyl]-ethoxy}-2-naphthoylguanidine dihydrochloride are obtained; m.p.: 269–271° C.

$^1$H-NMR (DMSO-d6): δ [ppm]=3.3 (4H), 3.7 (4H),3.9 (2H), 4.7 (2H), 7.0 (2H),7.3 (2H), 7.4 (1H), 7.6 (1H), 8.0 (2H), 8.2 (1H), 8.6 (2H), 8.0 (3H),11.4 (1H), 12.3 (1H).

EXAMPLE 8

4-Diethylaminoethyloxy-6-methoxy-1-methyl-2-naphthoyl-guanidine dihydrochloride

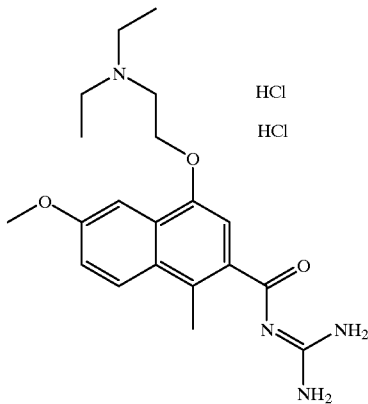

a) A mixture of 15 g (0.1 mol) of p-methoxyacetophenone and 29 g (0.2 mol) of dimethyl succinate dissolved in 100 ml of tert-butanol is added dropwise at 70° C. to a solution of 11.2 g (0.1 mol) of potassium tert-butoxide in 100 ml of tert-butanol. The mixture is heated at 70° C. for a further 4 h, then the reaction mixture is concentrated, treated with water and extracted twice with ethyl acetate. After acidifying the aqueous phase, the precipitated product is extracted with ethyl acetate and the extract is dried over $MgSO_4$ and concentrated in vacuo. The residue (21 g) is heated under reflux with 6.2 g (0.08 mol) of sodium acetate in 120 ml of acetic anhydride for 4 h. The mixture is concentrated in vacuo, the residue is treated with water, the mixture is extracted with ethyl acetate and the extract is washed with sodium carbonate solution. After concentration of the organic phase and purification by medium-pressure chromatography, 8.0 g of methyl 4-acetoxy-6-methoxy-1-methyl-2-naphthoate are obtained.

b) 7.5 g (26 mmol) of methyl 4-acetoxy-6-methoxy-1-methyl-2-naphthoate in 200 ml of methanol are stirred at room temperature for 30 min with 9.4 g (52 mmol) of 30 percent sodium methoxide solution. The mixture is concentrated, the residue is acidified with dilute hydrochloric acid and the mixture is extracted with ethyl acetate. After drying the organic phase over $MgSO_4$ and concentrating in vacuo, 4.1 g of methyl 4-hydroxy-6-methoxy-1-methyl-2-naphthoate are obtained.

c) 1.5 g (6.1 mmol) of methyl 4-hydroxy-6-methoxy-1-methyl-2-naphthoate and 0.49 g (9.1 mmol) of sodium methoxide are stirred at 40° C. under argon for 15 min in 25 ml of DMF. 1.4 g of diethylaminoethyl chloride are then added and the mixture is additionally stirred at 40° C. for 30 min. The DMF is stripped off on a rotary evaporator, the residue is taken up in dilute hydrochloric acid, and the mixture is extracted with ethyl acetate. The aqueous phase is rendered alkaline with sodium hydroxide solution and extracted with ethyl acetate again. After concentrating this extract, 1.8 g of crude methyl 4-diethylaminoethyloxy-6-methoxy-1-methyl-2-naphthoate are obtained, which is hydrolyzed directly to the acid by boiling for 2 hours with 1 g of KOH in 20 ml of methanol. After concentrating the reaction mixture, the residue is dissolved in 20 ml of water and acidified to pH 5.5 with concentrated hydrochloric acid, the product precipitating. 0.5 g of 4-diethylamino-ethyloxy-6-methoxy-1-methyl-2-naphthoic acid is obtained; m.p. 170° C.

d) 0.35 g of CDI are added to a suspension of 0.5 g of 4-diethylamino-ethyloxy-6-methoxy-1-methyl-2-naphthoic acid in 18 ml of THF, and the solution obtained is stirred at RT for 4 h. 0.44 g of guanidine is then added, the mixture is additionally stirred for 1.5 h and concentrated, and the residue is stirred with water. The precipitated product is filtered off with suction, and 0.23 g of 4-diethylaminoethyloxy-6-methoxy-1-methyl-2-naphthoylguanidine is obtained, m.p. 135° C., which can be converted with ethereal hydrochloric acid into the dihydrochloride, m.p. 235° C.

Pharmacological Data

Inhibition of the $Na^+/H^+$ Exchanger of Rabbit Erythrocytes

White New Zealand rabbits (Ivanovas) received a standard diet containing 2% cholesterol for six weeks in order to activate $Na^+/H^+$ exchange and thus to be able to determine the $Na^+$ influx into the erythrocytes via $Na^+/H^+$ exchange by flame photometry. The blood was taken from the auricular arteries and rendered uncoagulable by means of 25 IU/ml of potassium heparin. A part of each sample was used for the duplicate determination of the hematocrit by centrifugation. Aliquots of 100 µl in each case were used to measure the $Na^+$ starting content of the erythrocytes.

In order to determine the amiloride-sensitive sodium influx, 100 µl of each blood sample were incubated at pH 7.4 and 37° C. in 5 ml in each case of a hyperosmolar salt-sucrose medium (mmol/l: 140 NaCl, 3 KCl, 150 sucrose, 0.1 ouabain, 20 trishydroxymethylaminomethane). The erythrocytes were then washed three times with ice-cold $MgCl_2$—ouabain solution (mmol/l: 112 mg $MgCl_2$, 0.1 ouabain) and hemolyzed in 2.0 ml of distilled water. The intracellular sodium content was determined by flame photometry.

The net $Na^+$ influx was calculated from the difference between sodium starting values and the sodium content of the erythrocytes after incubation. The amiloride-inhibitable sodium influx ensued from the difference in the sodium content of the erythrocytes after incubation with and without amiloride $3 \times 10^{-4}$ mol/l. The sodium influx was also determined in this manner in the case of the compounds according to the invention.

What is claimed is:

1. A compound of the formula I

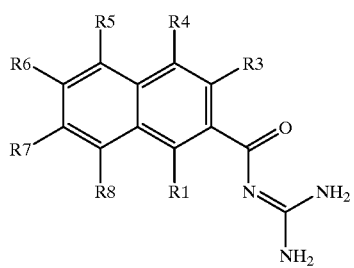

in which:
one of the substituents R1, R3, R4, R5, R6, R7 and R8 is $XY_aWZ$ or $X'Y_aWZ'$;
X is O, S, NR(10);
R(10) is H, alkyl having 1, 2, 3 or 4 carbon atoms;
Y is alkylene having 1, 2, 3, 4 or 5 $CH_2$ groups, where one of these $CH_2$ groups can be replaced by O, NR(13) or o-, p- or m-phenylene;
R(13) is H, alkyl having 1, 2, 3 or 4 carbon atoms;
a is zero or 1;
W is $CH_2$ or—if W does not immediately follow a heteroatom of the group $XY_a$—alternatively O or NR(14);
R(14) is H, alkyl having 1, 2, 3 or 4 carbon atoms;

Z is C(=O)R(15), or—if W is not O or NR(14)—alternatively NR(16)R(17);
R(15) is $N=C(NH_2)_2$, NR(18)R(19), $N(CH_2)_bNR(18)R(19)$ or OR(20);
b is 2 or 3;
R(18) and R(19) independently of one another are H or alkyl having 1, 2, 3, 4 or 5 carbon atoms; or
R(18) and R(19) together are 4 or 5 methylene groups, of which one $CH_2$ group can be replaced by oxygen, S, NH, N—$CH_3$ or N-benzyl;
R(20) is H or alkyl having 1, 2, 3, 4, 5 or 6 carbon atoms;
R(16) and R(17) independently of one another are H, alkyl having 1, 2, 3, 4 or 5 carbon atoms or perfluoroalkyl having 1 or 2 carbon atoms; or
R(16) and R(17) together are 4 or 5 methylene groups, of which one $CH_2$ group can be replaced by oxygen, S, NH, N—$CH_3$, N-benzyl or N-(p-chlorophenyl);
X' is C(=O)NR(30) or C(=O)O, where the linkage with the naphthalene ring in each case takes place via the left atom;
R(30) is H, alkyl having 1, 2, 3 or 4 carbon atoms;
Z' is C(=O)R(15) or a 5- or 6-membered N-containing aromatic heterocycle having up to 5 carbon atoms, where the 5- or 6-membered N-containing aromatic heterocycle is unsubstituted or substituted by 1–3 substituents selected from the group consisting of F, Cl, Br, $CF_3$, methyl, methoxy and NR(21)R(22);
R(21) and R(22) independently of one another are H or alkyl having 1, 2, 3 or 4 carbon atoms;
R(15) is $N=C(NH_2)_2$, NR(18)R(19), $N(CH_2)_bNR(18)R(19)$ or OR(20);
R(18) and R(19) independently of one another are H, alkyl having 1, 2, 3, 4 or 5 carbon atoms; or
R(18) and R(19) together are 4 or 5 methylene groups, of which one $CH_2$ group can be replaced by oxygen, S, NH, N—$CH_3$, or N-benzyl;
b is 2 or 3;
R(20) is H, alkyl having 1, 2, 3, 4, 5 or 6 carbon atoms; or
Z'—if W is not O or NR(14)—is NR(16) R(17);
R(16) and R(17) independently of one another are H or alkyl having 1, 2, 3, 4 or 5 carbon atoms; or
R(16) and R(17) together are 4 or 5 methylene groups, of which one $CH_2$ group can be replaced by oxygen, S, NH, N—$CH_3$, N-benzyl or N-(p-chlorophenyl);
and the other substituents R1, R3, R4, R5, R6, R7 and R8 in each case, which are still not allocated by the definitions given above, independently of one another are H, F, Cl, Br, I, CN, $NO_2$, $CF_3$ or $V_pQ_qU$;
V is O, $SO_2$, or C(=O)O;
p is zero or 1;
Q is alkylene having 1, 2, 3, 4, 5, 6, 7 or 8 $CH_2$ groups, where one of these $CH_2$ groups can be replaced by O, S, NR(68) or o-, p- or m-phenylene;
R(68) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms:
q is zero or 1;
U is H or alkyl having 1, 2, 3 or 4 carbon atoms;
but where at least one of the substituents R5, R6, R7 and R8 is not equal to hydrogen;
or its pharmaceutically tolerable salts.

2. A compound of the formula I as claimed in claim 2, in which:
  one of the substituents R1, R3, R4, R5, R6, R7 and R8 is $XY_aWZ$ or $X'Y_aWZ'$;
  X is O;
  Y is alkylene having 1, 2, 3, 4 or 5 $CH_2$ groups, where one of these $CH_2$ groups can be replaced by o-, p- or m-phenylene;
  a is zero or 1;
  W is $CH_2$ or—if W does not immediately follow a heteroatom of the group $XY_a$—alternatively O or NR(14);
  R(14) is H or methyl;
  Z is C(=O)R(15), or—if W is not O or NR(14)—alternatively NR(16)R(17);
    R(15) is $N=C(NH_2)_2$, NR(18)R(19), or OR(20);
      R(18) and R(19) independently of one another are H or alkyl having 1, 2, 3 or 4 carbon atoms; or
      R(18) and R(19) together are 4 or 5 methylene groups, of which one $CH_2$ group can be replaced by oxygen, NH, N—$CH_3$ or N-benzyl;
      R(20) is H or alkyl having 1, 2, or 3 carbon atoms;
    R(16) and R(17) independently of one another are H or alkyl having 1, 2, 3, or 4 carbon atoms;
    R(16) and R(1 7) together are 4 or 5 methylene groups, of which one $CH_2$ group can be replaced by oxygen, S, NH, N—$CH_3$, N-benzyl or N-(p-chlorophenyl);
  X' is C(=O)NR(30) or C(=O)O; where the linkage with the naphthalene ring in each case takes place via the left atom;
    R(30) is H or methyl;
  Z' is C(=O)R(15) or a 5- or 6-membered N-containing aromatic heterocycle having up to 5 carbon atoms;
    R(15) is $N=C(NH_2)_2$, NR(18)R(19) or OR(20);
      R(18) and R(19) independently of one another are H or alkyl having 1, 2, 3, or 4 carbon atoms; or
      R(18) and R(19) together are 4 or 5 methylene groups, of which one $CH_2$ group can be replaced by oxygen, NH, N—$CH_3$, or N-benzyl;
      R(20) is H or alkyl having 1, 2 or 3 carbon atoms; or
  Z'—if W is not O or NR(14)—is NR(16) R(17);
    R(16) and R(17) independently of one another are H or alkyl having 1, 2, 3 or 4 carbon atoms; or
    R(16) and R(17) together are 4 or 5 methylene groups, of which one $CH_2$ group can be replaced by oxygen, S, NH, N—$CH_3$, or N-benzyl;
and the other substituents R1, R3, R4, R5, R6, R7 and R8 in each case, which are still not allocated by the definitions given above,
  independently of one another are H, F, Cl, Br, I, $CF_3$ or $V_pQ_qU$;
  V is O, $SO_2$, or C(=O)O;
  p is zero or 1;
  q is zero;
  U is H or alkyl having 1, 2, 3 or 4 carbon atoms;
but where at least one of the substituents R5, R6, R7 and R8 is not equal to hydrogen.

3. A compound of the formula I as claimed in claim 2 in which the compound is 6-(2-diethylaminoethoxy)-2-naphthoylguanidine.

4. A compound of the formula I as claimed in claim 2 in which the compound is 6-(2-diethylaminoethoxy)-2-naphthoylguanidine dihydrochloride.

5. A compound of the formula I as claimed in claim 2 in which the compound is 6-(2-Diisopropylaminoethoxy)-2-naphthoylguanidine.

6. A compound of the formula I as claimed in claim 2 in which the compound is 6-(2-Diisopropylaminoethoxy)-2-naphthoylguanidine dihydrochloride.

7. A compound of the formula I as claimed in claim 2 in which the compound is 6-[2-(4-Morpholinyl)ethoxy]-2-naphthoylguanidine.

8. A compound of the formula I as claimed in claim 2 in which the compound is 6-[2-(4-Morpholinyl)ethoxy]-2-naphthoylguanidine dihydrochloride.

9. A compound of the formula I as claimed in claim 2 in which the compound is 6-(Guanidinocarbonylmethoxy)-2-naphthoylguanidine.

10. A compound of the formula I as claimed in claim 2 in which the compound is 6-(Guanidinocarbonylmethoxy)-2-naphthoylguanidine dihydrochloride.

11. A compound of the formula I as claimed in claim 2 in which the compound is 6-(3-Pyridylmethylaminocarbonyl)-2-naphthoylguanidine.

12. A compound of the formula I as claimed in claim 2 in which the compound is 6-(3-Pyridylmethylaminocarbonyl)-2-naphthoylguanidine dihydrochloride.

13. A compound of the formula I as claimed in claim 2 in which the compound is 6-[2-(Guanidinocarbonyloxy)ethylaminocarbonyl]-2-naphthoylguanidine.

14. A compound of the formula I as claimed in claim 2 in which the compound is 6-[2-(Guanidinocarbonyloxy)ethylaminocarbonyl]-2-naphthoylguanidine dihydrochloride.

15. A compound of the formula I as claimed in claim 2 in which the compound is 6-{2-[4-(4-Chlorophenyl)-1-piperazinyl]-ethoxy}-2-naphthoylguanidine.

16. A compound of the formula I as claimed in claim 2 in which the compound is 6-{2-[4-(4-Chlorophenyl)-1-piperazinyl]-ethoxy}-2-naphthoylguanidine dihydrochloride.

17. A compound of the formula I as claimed in claim 2 in which the compound is 4-Diethylaminoethyloxy-6-methoxy-1-methyl-2-naphthoylguanidine.

18. A compound of the formula I as claimed in claim 2 in which the compound is 4-Diethylaminoethyloxy-6-methoxy-1-methyl-2-naphthoylguanidine dihydrochloride.

19. A pharmaceutical composition comprising an effective amount of a compound of the formula I as claimed in claim 2.

20. A method of treating arrhythmias comprising administering an effective amount of a compound I as claimed in claim 2.

21. A method of treating or prophylaxis of cardiac infarct comprising administering an effective amount of a compound I as claimed in claim 2.

22. A method of treating or prophylaxis of angina pectoris comprising administering an effective amount of a compound I as claimed in claim 2.

23. A method of treating or prophylaxis of ischemic conditions of the heart comprising administering an effective amount of a compound I as claimed in claim 2.

24. A method of treating or prophylaxis of ischemic conditions of the peripheral vessels comprising administering an effective amount of a compound I as claimed in claim 2.

25. A method of treating or prophylaxis of ischemic conditions of the central nervous system comprising administering an effective amount of a compound I as claimed in claim 2.

26. A method of treating or prophylaxis of stroke comprising administering an effective amount of a compound I as claimed in claim 2.

27. A method of treating or prophylaxis of ischemic conditions of the periphral organs and members comprising administering an effective amount of a compound I as claimed in claim 2.

28. A method of treating of states of shock comprising administering an effective amount of a compound I as claimed in claim 2.

29. A method of lowering a total serum cholesterol level comprising administering an effective amount of a compound I as claimed in claim 1.

30. A method of lowering a serum concentration of VLDL, LDL, or both VLDL and LDL, comprising administering an effective amount of a compound I as claimed in claim 1.

* * * * *

UNITED STATES PATENT AND TRADEMARK OFFICE
CERTIFICATE OF CORRECTION

PATENT NO.: 6,087,304
DATED: July 11, 2000
INVENTORS: Joachim BRENDEL et al.

It is certified that an error appears in the above-identified patent and that said Letters Patent is hereby corrected as shown below:

On the Title Page, Item [75], in the Inventors, line 1, "Vibel" should read --Vilbel--.
In Claim 1, col. 19, line 58, "or4" should read --or 4--.
In Claim 2, col. 21, line 1, "claim 2" should read --claim 1--.
In Claim 2, col. 21, line 24, after "atoms;", insert --or--.
In Claim 3, col. 21, line 58, "claim 2" should read --claim 1--.
In Claim 4, col. 21, line 61, "claim 2" should read --claim 1--.
In Claim 5, col. 21, line 65, "claim 2" should read --claim 1--.
In Claim 6, col. 22, line 1, "claim 2" should read --claim 1--.
In Claim 7, col. 22, line 4, "claim 2" should read --claim 1--.
In Claim 8, col. 22, line 7, "claim 2" should read --claim 1--.
In Claim 9, col. 22, line 10, "claim 2" should read --claim 1--.
In Claim 10, col. 22, line 13, "claim 2" should read --claim 1--.
In Claim 11, col. 22, line 16, "claim 2" should read --claim 1--.
In Claim 12, col. 22, line 20, "claim 2" should read --claim 1--.
In Claim 13, col. 22, line 23, "claim 2" should read --claim 1--.
In Claim 14, col. 22, line 26, "claim 2" should read --claim 1--.
In Claim 15, col. 22, line 30, "claim 2" should read --claim 1--.
In Claim 16, col. 22, line 33, "claim 2" should read --claim 1--.
In Claim 17, col. 22, line 37, "claim 2" should read --claim 1--.
In Claim 18, col. 22, line 41, "claim 2" should read --claim 1--.

UNITED STATES PATENT AND TRADEMARK OFFICE
CERTIFICATE OF CORRECTION

PATENT NO.: 6,087,304

DATED: July 11, 2000

INVENTORS: Joachim BRENDEL et al.

It is certified that an error appears in the above-identified patent and that said Letters Patent is hereby corrected as shown below:

In Claim 19, col. 22, lines 45-46, "claim 2" should read --claim 1--.
In Claim 20, col. 22, line 49, "claim 2" should read --claim 1--.
In Claim 21, col. 22, line 52, "claim 2" should read --claim 1--.
In Claim 22, col. 22, line 55, "claim 2" should read --claim 1--.
In Claim 23, col. 22, line 58, "claim 2" should read --claim 1--.
In Claim 24, col. 22, lines 62-63, "claim 2" should read --claim 1--.
In Claim 25, col. 22, line 67, "claim 2" should read --claim 1--.
In Claim 26, col. 23, line 3, "claim 2" should read --claim 1--.
In Claim 27, col. 23, line 5, "periphral" should read --peripheral--.
In Claim 27, col. 23, line 7, "claim 2" should read --claim 1--.
In Claim 28, col. 23, line 10, "claim 2" should read --claim 1--.

Signed and Sealed this

Twenty-ninth Day of May, 2001

Attest:

NICHOLAS P. GODICI

Attesting Officer

Acting Director of the United States Patent and Trademark Office